United States Patent [19]

Shillington et al.

[11] Patent Number: 5,573,113
[45] Date of Patent: Nov. 12, 1996

[54] NEEDLE REMOVAL DEVICE FOR BLOOD COLLECTION HOLDERS

[75] Inventors: Richard A. Shillington, Leucadia; Kenneth R. McCord, Encinitas, both of Calif.

[73] Assignee: Med-Safe Systems, Inc., Oceanside, Calif.

[21] Appl. No.: 367,594

[22] Filed: Jan. 3, 1995

[51] Int. Cl.$^6$ .................................................. B65D 85/20
[52] U.S. Cl. ............................ 206/366; 29/240; 206/370
[58] Field of Search ..................... 29/239, 240; 206/366, 206/370; 604/110

[56] References Cited

U.S. PATENT DOCUMENTS

| | | | |
|---|---|---|---|
| 4,798,587 | 1/1989 | Willoughby | 604/110 |
| 4,807,344 | 2/1989 | Kelson et al. | 29/240 |
| 4,986,811 | 1/1991 | Thead et al. | 604/110 |
| 5,188,598 | 2/1993 | Thead et al. | 206/366 |
| 5,312,346 | 5/1994 | Han | 604/110 |

*Primary Examiner*—Jimmy G. Foster
*Attorney, Agent, or Firm*—Baker, Maxham, Jester & Meador

[57] ABSTRACT

A needle removal apparatus, comprises a support member having a throughbore, a tubular sleeve reciprocally mounted in the throughbore for movement from an outermost position to an innermost position, a spring normally biasing the sleeve to the outermost position, a helical slot for constraining the sleeve to rotate during movement between the outermost position and the innermost positions, and a coupling at an inner end of the sleeve for coupling to a needle hub for unthreading the needle hub from an end of a tubular barrel during movement with the sleeve to the innermost position.

22 Claims, 2 Drawing Sheets

NEEDLE REMOVAL DEVICE FOR BLOOD COLLECTION HOLDERS

BACKGROUND OF THE INVENTION

The present invention relates to needle removal devices for syringes and other holders and pertains particularly to an improved extractor for quick and easy removal of needles from holders.

A huge volume of hypodermic needles are used daily in the medical and health care industry and must be disposed of safely. These used needles pose a major health problem to the medical personnel using them as well as others who may come into contact with them. The safe and effective disposal of these hypodermic needles poses one of the greatest health and disposal problems for the medical and health care industry.

Hypodermic needles are widely used for both injection of medication and for withdrawing blood samples for diagnostic purposes. In many cases the needle is removed from the holder and separately disposed of. In some cases, particularly certain blood drawing devices, the holder is reused. In these cases, it is essential that the needle be easily, quickly and safely removed without risk to the user.

The present common technique of drawing blood samples is by means of an evacuated tube and holder combination such as that sold under the trademark VACUTAINER by the Becton Dickinson Company. These blood collection assemblies comprise a tubular holder or barrel having a double needle on one end and receives an evacuated tubular chamber. The needle is threadably mounted on one end of the tubular holder with an exterior needle for penetrating the patient tissue for receiving blood. The interior needle is covered with a sheath valve and penetrates an elastomeric stopper in one end of a vacuum tube to draw the blood.

Many devices have been proposed in the past for removal and disposal of the needles. Examples of these are disclosed in the following patents:

| | |
| --- | --- |
| Shillington | 4,667,821 |
| Shillington | 4,984,686 |
| Thead et al. | 4,986,811 |
| Sagstetter et al. | 5,086,922 |
| Sagstetter et al. | 5,092,462 |
| Shillington | 5,249,680 |

These prior art devices are generally effective to remove the needles. However, they all have various drawbacks for example, most of them require the use of both hands.

It is desirable that a simple, safe and effective quick release needle holder for hypodermic needles be available.

SUMMARY OF THE INVENTION

In accordance with a primary aspect of the present invention a needle removal apparatus, comprises a support member having a throughbore, a tubular sleeve reciprocally mounted in said throughbore for movement from an outermost position to an innermost position, biasing means for normally biasing said sleeve to the outermost position, helical means for constraining said sleeve to rotate during movement between said outermost position and said innermost position, and coupling means at an inner end of said sleeve for coupling to a needle hub for unthreading said needle hub from an end of a tubular barrel during movement with said sleeve to said innermost position.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
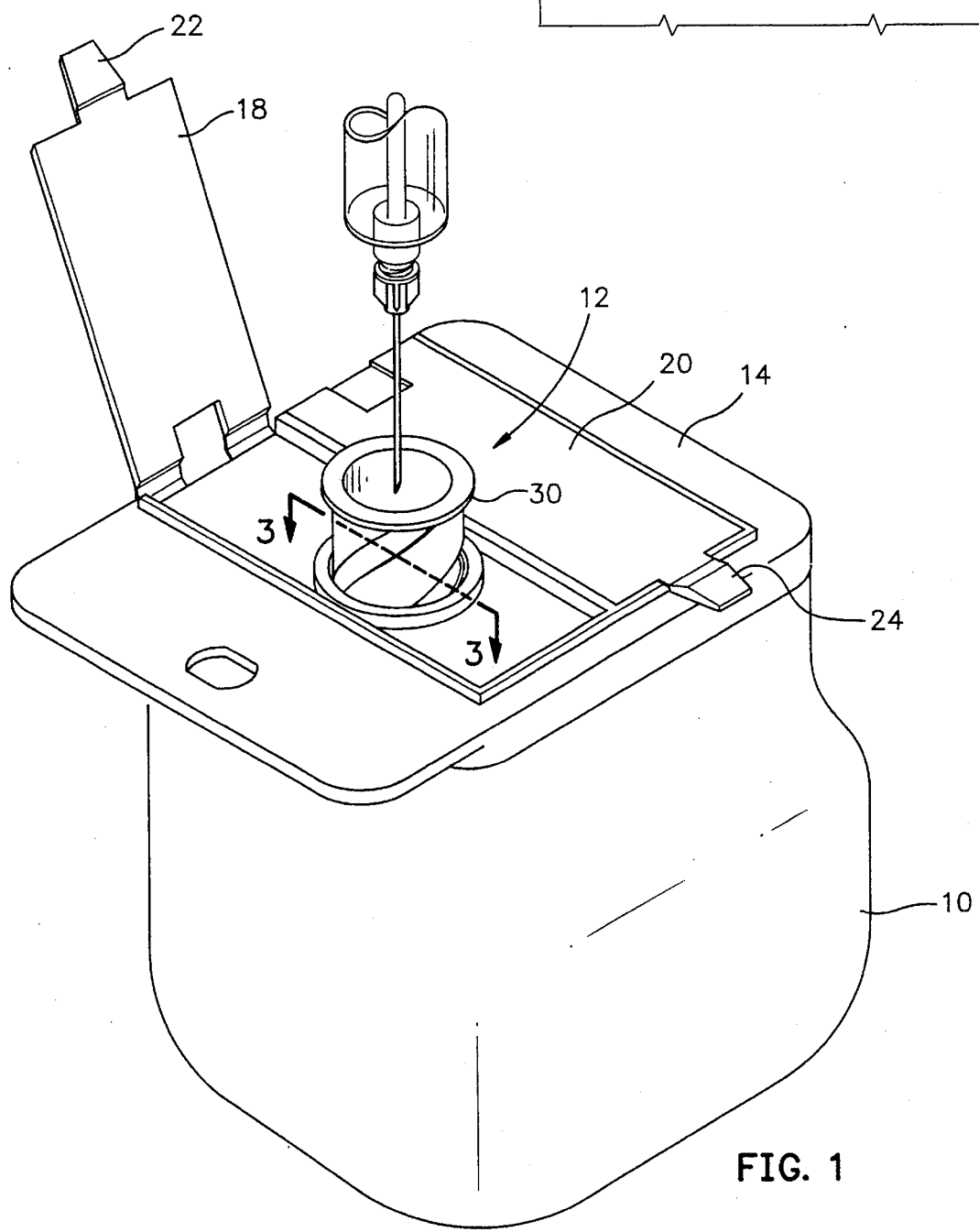
FIG. 1 is a perspective view of an exemplary embodiment of the present invention embodied in a disposable container.
Figure 2:
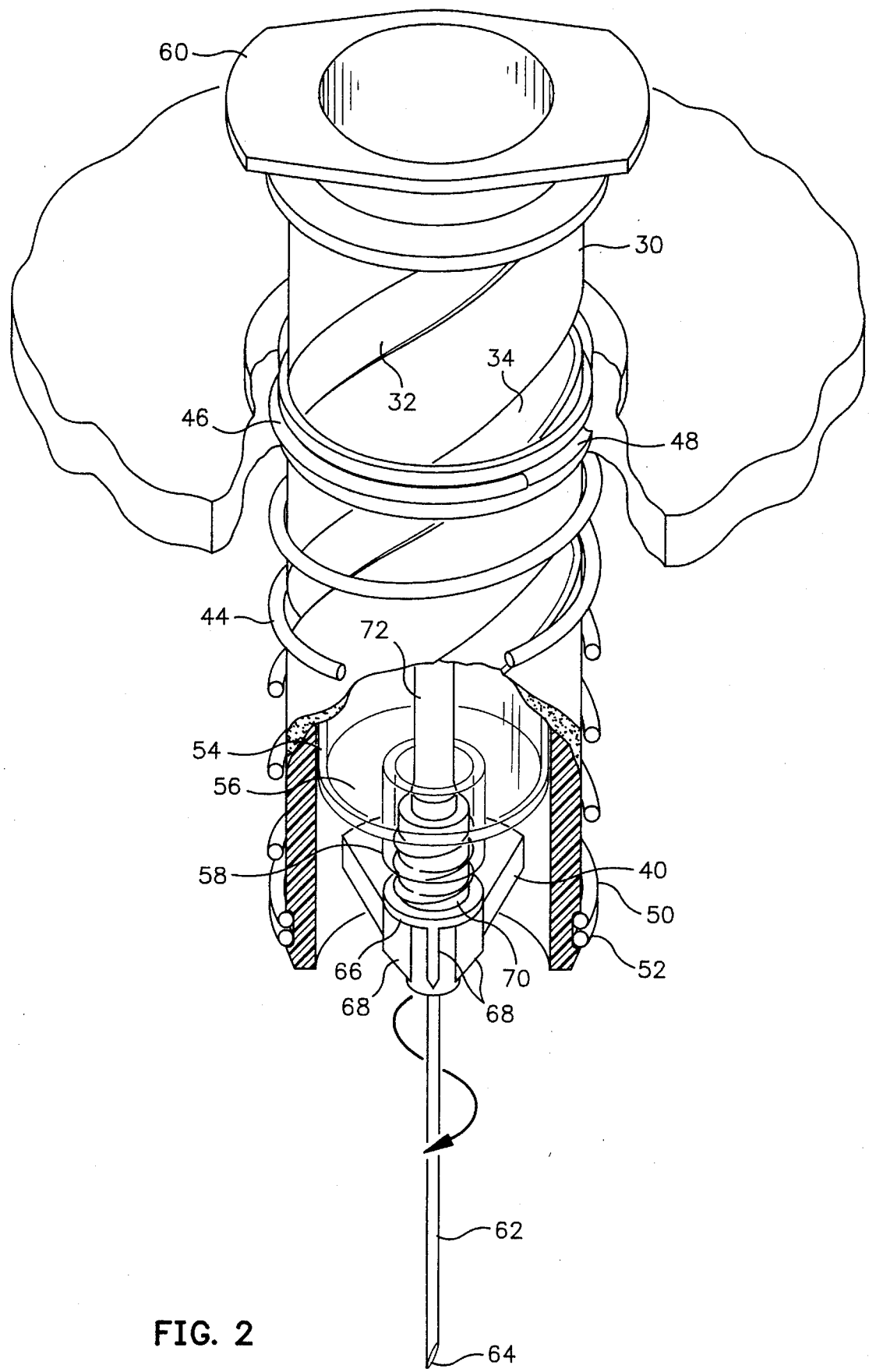
FIG. 2 is a perspective view of the needle removal device of FIG. 1, with portions broken away to reveal details.

Referring now to the drawings, and particularly to FIG. 1, there is illustrated a disposable sharps container which embodies a needle removal apparatus designated generally at 12, constructed in accordance with a preferred embodiment of the present invention. This container has a closure assembly which comprises a top support or frame member 14 which in the illustrated embodiment has a generally rectangular configuration for mounting on and covering the upwardly opening open top of a disposable container of a traditional construction. This top is permanently attached to a plastic type disposable container 10 of the type typically used for the disposal of syringes, sharps and the like. These containers are disclosed in a number of prior patents assigned to the assignee hereof.

The needle removal apparatus is in the closure frame 14 which preferably also has an opening (not shown) for the disposal of syringes and holders with covers 18 and 20 for covering the needle extraction apparatus and the opening. This needle removal device or apparatus may also be incorporated into any number of other container closure assemblies associated with various container closures, such as disclosed, for example, in U.S. Pat. No. 4,984,686.

The illustrated closure assembly is designed for use in conjunction with containers for the disposal of vacuum type syringes widely used for the drawing of blood samples. In the illustrated embodiment the opening and the needle removal apparatus 12 are positioned within a rectangularly recessed portion, as illustrated with the hinged cover members 18 and 20 hinged to one side of the top frame. The hinge covers are shown with 18 pivoted to an open position, with each including locking tabs 22 and 24 for engaging slots in the closure for latching them in a permanently closed position when the container is filled and ready for disposal.

Figure 3:
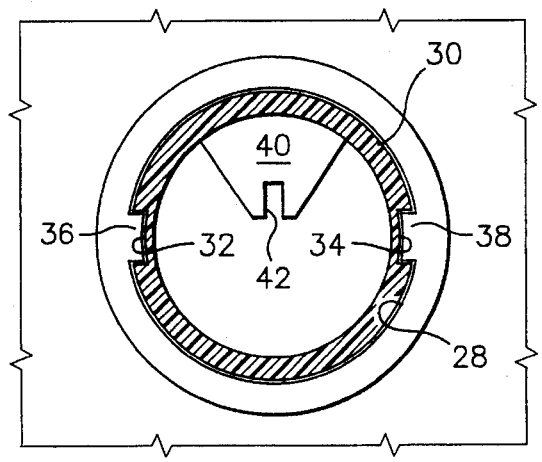
FIG. 3 is a section view taken generally on 3—3 of FIG. 1.

The closure frame serves as a support member and, as shown in FIG. 3, includes a throughbore 28 for receiving and reciprocally mounting an elongated tubular sleeve 30 having a pair of helical grooves 32 and 34. The throughbore may be formed of or by an elongated sleeve for guiding the sleeve 30 if desired. The helical grooves 32 and 34 spiral along the outer surface of the tubular sleeve 30 and are engaged by a pair of opposed followers 36 and 38. These followers and helical grooves constrain the tubular sleeve to rotate as it is reciprocated within the throughbore. The helical grooves must cause the sleeve to rotate a sufficient times to completely unthread the needle. Typically less than a full rotation is required.

The tubular sleeve 30 extends downward into the container and is formed at the bottom end with a needle ejector coupling comprising an inwardly (toward the axis) extending partial wall 40 that extends from the interior wall of the tube inward towards the center axis and includes a slot 42 for receiving a spline on the hub of a needle. This couples to the hub of the needle and upon rotation of the sleeve unthreads the needle from the barrel of the holder. The coupling may take any form to accommodate the needle designed. The sleeve is normally biased to its uppermost position by means of a coil spring 44 secured at an upper end 46 to the support member and at the bottom end 48 to the sleeve by means of a groove 50. Any suitable spring or biasing means may be utilized.

The tubular sleeve in the illustrated embodiment is sized in length and diameter to receive a vacuum tube type syringe such as that sold under the trademark VACUTAINER. However, it may be sized and designed for any syringe body. The blood collection holder comprises an elongated cylindrical tube 54 having a lower end 56 with a forwardly projecting internally threaded socket 58 for receiving the threaded hub of a needle. The upper end of the holder barrel is provided with finger flanges 60. The term needle holder as used herein is intended to include any type syringe or other body that couples to and holds or supports a needle for use.

A typical needle for such blood collection devices comprises an elongated steel cannula 62 having a sharpened point 64 at one end with a hub 66 intermediate the ends of the cannula. The hub 66 includes a plurality of splines 68 on one side (external side) of the central hub and external threaded section 70 on the other (inner) side. The opposite end of the needle is similarly provided with a sharp point not shown and covered by a elastomeric sheath 70, such as silicone which serves as a valve to cover the inner end of the needle when not extending into a stopper on the end of a vacuum tube.

In operation, the needle removal or extraction apparatus is exposed and projects upward from the top of the container. When it is desired to remove the needle from a holder, the holder is inserted downward into the tubular sleeve such that a spline on the needle hub engages in slot 42, thereby coupling the needle hub directly to the tubular sleeve. The finger flange end of the holder barrel is held against rotation and is pressed downwardly axially along its center axis forcing the sleeve downward resulting in rotation of the sleeve and concurrently therewith the rotation of the hub 66 of the needle and threading it from the socket 58 of the needle holder. The needle becomes unthreaded from the socket and drops into the disposable container. The holder 54 is then removed from the needle removal apparatus and either reused, if desired, or disposed of by inserting into the other opening in the top of the container.

While we have illustrated and described our invention by means of specific embodiments, it is to be understood that numerous changes and modifications may be made therein without departing from the spirit and scope of the invention as defined by the claims.

I claim:

1. A needle removal apparatus, comprising:

a support member having a generally planar top surface and a throughbore defined by structure extending entirely below said top surface, said top surface being normally horizontal in use;

an elongated tubular sleeve having an inner end and an outer end, said sleeve reciprocally mounted in said throughbore for movement from an outermost position, wherein a portion of said sleeve including said outer end extends above said top surface, to an innermost position wherein most of the sleeve portion is substantially below said top surface and said outer end is adjacent said top surface;

biasing means for normally biasing said sleeve to the outermost position;

a helical groove formed in an outer surface of said sleeve;

a follower member fixed to said support member at said throughbore and engaging said helical groove for constraining said sleeve to rotate during movement between said outermost position and said innermost position; and coupling means on said inner end of said sleeve for direct coupling to a needle hub for unthreading said needle hub from an end of a tubular barrel during movement with said sleeve toward said innermost position.

2. An apparatus according to claim 1 wherein said support member is a portion of a disposable container housing.

3. An apparatus according to claim 1 wherein said coupling means comprises a slot for receiving a spline on a hub of a needle.

4. An apparatus according to claim 3 comprising a separate helical groove on each side of said sleeve, and pair of separate spaced apart opposed ones of said follower members engaging said grooves.

5. An apparatus according to claim 1 wherein said frame assembly includes a cover pivotally mounted on said top surface and pivotally moveable to a position covering said throughbore.

6. An apparatus according to claim 5 wherein said frame assembly, said structure defining said throughbore and said followers are defined by an integral unitary structure; and said inwardly projecting flange and said for coupling to a needle hub are on an inner surface of and integral with said sleeve.

7. An apparatus according to claim 1 wherein said frame assembly, said structure defining said throughbore and said followers are defined by an integral unitary structure; and said means for coupling to a needle hub are on an inner surface of and integral with said sleeve.

8. An apparatus according to claim 7 wherein said means for coupling comprises a slot for receiving a spline on a hub of a needle.

9. An apparatus according to claim 8 wherein said biasing means comprises a coil spring in tension.

10. An apparatus according to claim 7 wherein said biasing means comprises a coil spring in tension.

11. A needle removal apparatus comprising:

a support member having a throughbore;

a tubular sleeve reciprocally mounted in said throughbore for movement from an outermost position to an innermost position;

biasing means comprising a coil spring in tension for normally biasing said sleeve to the outermost position;

helical means comprising a separate helical groove on each side of said sleeve, and pair of spaced apart opposed followers engaging said grooves for constraining said sleeve to rotate during movement between said outermost position and said innermost position; and coupling means at an inner end of said sleeve comprising a slot for receiving a spline on a hub of a needle for coupling to a needle hub for unthreading said needle hub from an end of a tubular barrel during movement with said sleeve to said innermost position.

12. An apparatus according to claim 11 wherein said coupling means comprises a wall portion extending from an inner surface of said sleeve toward a central longitudinal axis of said sleeve and said slot formed in said wall for receiving a spline on a hub of a needle.

13. An apparatus according to claim 11 wherein said support member is a closure structure for a disposable container.

14. A needle removal apparatus for a disposable container, comprising:

frame means for mounting on an opening defined by a peripheral rim of a substantially rigid container;

said frame means having a throughbore;

a tubular sleeve having a central axis reciprocally mounted in said throughbore movement from an outermost position to an innermost position;

biasing means for normally biasing said sleeve to the outermost position;

a helical groove formed in opposite sides of said sleeve;

a pair of followers on said frame means for engaging said helical grooves and constraining said sleeve to rotate during movement between said outermost position and said innermost position; and an inwardly projecting flange mounted within an inner end of said sleeve, being adapted to revolve about the central axis of the sleeve as it moves from the outermost position to the innermost position and having a slot for direct coupling to a needle hub for unthreading said needle hub from an end of a tubular barrel during movement with said sleeve to said innermost position.

15. A needle removal apparatus for a disposable container, comprising:

frame means for mounting on an opening defined by a peripheral rim of a substantially rigid container;

said frame means having a throughbore;

a tubular sleeve reciprocally mounted in said throughbore for movement from an outermost position to an innermost position;

biasing means for normally biasing said sleeve to the outermost position;

a helical groove formed in opposite sides of said sleeve;

a pair of followers on said frame means for engaging said helical grooves and constraining said sleeve to rotate during movement between said outermost position and said innermost position; and an inwardly projecting flange at an inner end of said sleeve having a slot for coupling to a needle hub for unthreading said needle hub from an end of a tubular barrel during movement with said sleeve to said innermost position wherein said biasing means comprises a coil spring in tension between said frame means and said sleeve.

16. A needle removal for use in combination with a disposable container, comprising:

a closure frame assembly for mounting in an opening defined by a peripheral rim of a substantially rigid disposable container;

a throughbore in said frame for normally communicating with the interior of the container;

a tubular sleeve reciprocally mounted in said throughbore for movement from an outermost position to an innermost position, the sleeve having an inner end opening into the interior of the container;

biasing means comprising a coil spring in tension between said frame means and said sleeve for normally biasing said sleeve to the outermost position;

a helical groove formed in each side of said sleeve;

a pair of followers on said frame at said throughbore for engaging said helical grooves for constraining said sleeve to rotate during movement between said outermost 9 position and said innermost position; and an inwardly projecting flange at said inner end of said sleeve having means for coupling to a needle hub for unthreading said needle hub from an end of a tubular barrel during movement with said sleeve to said innermost position.

17. An apparatus according to claim 16 wherein said coupling means comprises a slot for receiving a spline on a hub of a needle.

18. An apparatus according to claim 16 wherein:

said frame assembly has a generally planar top surface and said throughbore is defined by structure disposed entirely below said top surface; and said tubular sleeve has an inner end and an outer end, said sleeve is reciprocally mounted in said throughbore with said outer end above said top surface and said inner end below said top surface for movement from said outermost position wherein a portion of said sleeve including said outer end extends above said top surface to said innermost position wherein said sleeve is substantially below said top surface.

19. An apparatus according to claim 16 wherein said frame assembly includes a cover pivotally mounted on said top surface pivotally moveable to a position covering said throughbore.

20. An apparatus according to claim 16 wherein said coupling means comprises a wall portion extending from an inner surface of said sleeve toward a central longitudinal axis of said sleeve and said slot is formed in said wall for receiving a spline on a hub of a needle.

21. An apparatus according to claim 16 wherein said frame assembly, said structure defining said throughbore and said followers are defined by an integral unitary structure; and said inwardly projecting flange and said for coupling to a needle hub are on an inner surface of and integral with said sleeve.

22. An apparatus according to claim 21 wherein said means for coupling comprises a slot for receiving a spline on a hub of a needle.

* * * * *